United States Patent [19]

Allan et al.

[11] 4,388,352
[45] Jun. 14, 1983

[54] METHOD FOR PREPARING A CONTROLLED RELEASE COMPOSITION

[75] Inventors: George G. Allan, Seattle, Wash.; Young C. Ko, Stockholm, Sweden

[73] Assignee: Board of Regents, University of Washington, Seattle, Wash.

[21] Appl. No.: 289,302

[22] Filed: Aug. 3, 1981

[51] Int. Cl.³ .................. B05D 3/02; D21D 3/00; D21F 11/00; A01N 37/38
[52] U.S. Cl. .................. 427/391; 71/DIG. 1; 71/117; 162/100; 162/158; 424/19; 424/22
[58] Field of Search .................. 162/158, 100; 71/DIG. 1, 117; 424/19, 22; 427/389.9, 391

[56]  References Cited
U.S. PATENT DOCUMENTS

| | | | |
|---|---|---|---|
| 3,137,631 | 6/1964 | Soloway | 162/158 X |
| 3,172,752 | 3/1965 | Pierce | 71/DIG. 1 |
| 3,697,371 | 10/1972 | Schleicher et al. | 162/158 X |
| 3,808,093 | 4/1974 | Hedstrom | 162/100 |

Primary Examiner—Michael R. Lusignan
Attorney, Agent, or Firm—Seed, Berry, Vernon & Baynham

[57] ABSTRACT

Controlled release compositions are made by a distillation method to include chemical impregnants (such as animal repellants, pesticides, herbicides, fungicides, plant growth stimulants, perfumes and deodorizers, fertilizers, and drugs) in biodegradable, microporous structures. Each microporous structure collapses upon drying but swells upon rewetting to allow the impregnant entrapped in it to diffuse from the structure. Never-dried wood pulp is a particularly desirable microporous structure because it has large pores initially, a large surface area initially, and demonstrated swelling capability. The method is particularly useful when the impregnant is insoluble in the fluid initially within the microporous structure and when the solvent for the impregnant is immiscible with that fluid.

14 Claims, No Drawings

METHOD FOR PREPARING A CONTROLLED RELEASE COMPOSITION

DESCRIPTION

Technical Field

This invention relates to a novel method for preparing a controlled release composition. In particular, this invention relates to entrapping an impregnant in the pores of never-dried α-cellulose pulp before the pores collapse upon drying by distilling a solution of the impregnant into the pores.

BACKGROUND ART

Controlled release compositions are being recognized as the technology of the future to provide continuing activity over an extended period of time without the need for additional applications of the active agent. Controlled release compositions are useful with animal repellants, pesticides, herbicides, fungicides, plant growth stimulants, fertilizers, and drugs. Controlled release compositions allow application of a lesser amount of active agent to achieve better control than application of the active agent directly (which generally results in loss through leaching or otherwise before the active agent can be effectively used). Four mechanisms are commonly employed to obtain controlled release:

(1) desorption from strong sorbents, like silica gel, mica, and activated charcoal;
(2) diffusion;
(3) erosion of biodegradable barrier materials; and
(4) release after retrograde chemical reactions, such as hydrolysis, thermodynamic dissociation, or microbial degradation.

The delivery rate of a chemical from a controlled release system is primarily influenced by the architecture of the system, the properties of the impregnant and of the rate-controlling matrix, and the driving force liberating the impregnant from the matrix. Physical controlled release compositions are either reservoir systems or monolithic systems. In a reservoir system, the active agent is encapsulated within a rate-controlling membrane. The membrane permeability and the membrane configuration determine the release rate. In a monolithic system, the active agent is dissolved or dispersed throughout a matrix, such as a polymer.

One commercial reservoir system uses a hollow fiber to hold the active agent, such as an insect pheromone. The release of the active agent from the fiber is diffusion controlled. This system is beneficial for volatile liquids, yet it is expensive because of the cost of manufacture of the tubes. Many other controlled-release compositions are known, especially for insecticides, drugs, and fertilizers. Most are encapsulation reservoir systems similar to the hollow fibers but depending on diffusion through a semipermeable membrane.

When cellulose is swollen in water and the water is replaced by a solvent through a series of solvent exchanges, the final solvent is often trapped inside the cellulose structure upon its drying. The entrapped solvent is released by contacting the cellulose with water. Kistler, 35 *J. Phys. Chem.* 52 (1932).

Because investigators have been interested primarily in enhancing the rates of chemical reactions by making inclusion cellulose, no systematic study of the inclusion process has been conducted. Believing that the solvents were entrapped in the amorphous or intercrystalline regions of the cellulose stucture, most investigators thought that the molecular size of the solvents used must be small (less than about 10 angstroms). Blackwell, Kolpak, and Gardner, *Cellulose Chemistry and Technology*, 48 ACS Symp. Ser. 42 (1977). The release mechanism was thought to include destruction of the crystalline region of the cellulose during swelling. Small amounts of chemical solvents, such as ethylene glycol, methanol, ethanol, acetone, toluene, benzene, carbon tetrachloride, pyridine, n-hexane, chloroform, cyclohexane, isopropanol, n-butanol, bromobenzene, and dichloroethane, were released using water, ammonia, or sodium hydroxide as a swelling agent.

DISCLOSURE OF INVENTION

A method for preparing a controlled release composition uses distillation instead of multiple solvent exchange stages to entrap an impregnant within the pores of a microporous carrier. The method is particularly useful when the impregnant is substantially insoluble in the fluid which initially fills the carrier's pores, and when the solvent in which the impregnant is reasonably soluble is immiscible with the fluid in the pores. In these circumstances, distillation of the fluid from a mixture of the carrier, solvent, and impregnant readily allows the diffusion of impregnant into the pores. The fragile pores are not as damaged as in solvent exchange and filtration; impregants of larger molecular size may be used.

The method generally comprises the steps of (1) immersing a carrier, such as never-dried cellulose pulp, in a solution of impregnant, (2) distilling the mixture to exchange fluid in the pores of the carrier with the solution, and (3) drying of the carrier to entrap the impregnant within its pores. Adding a surfactant to the mixture lowers the interfacial tension between the fluid in the pores and the solvent and enhances the entrapment of impregnant.

BEST MODE FOR CARRYING OUT THE INVENTION

The never-dried pulp has much larger lamellar pores than "once-dried" pulp. This invention capitalizes on the structural differences in the two types of pulp to prepare an improved controlled release composition by a distillation method.

The controlled release compositions of this invention are easy to make from economical components. They are useful for a wide variety of applications, including release of plant growth stimulants, herbicides, pesticides, fungicides, perfumes or deodorizers, animal repellants, drugs, fertilizers, and the like. When never-dried wood pulp is used as the carrier for one of these impregnants, release is diffusion controlled with a pseudo first-order rate constant.

Never-dried pulp is formed by removing the lignin and hemicellulose from wood fibers during pulping by any of the well-recognized pulping processes. The pulp obtained is a composite of several hundred concentric lamellae of cellulose microfibrils. Each lamella is separated from the others by water-filled spaces (pores) which vary in width from about 25–300 angstroms. The larger spaces are located nearer the periphery, with the narrower toward the lumen (a central channel of about 10–20μ width). The spacing more or less corresponds to the thickness of the lignin in the wood fiber. The pore size has a generally log normal distribution; that is, a plot of the logarithm of the pore size against frequency has a generally Gaussian distribution. The never-dried pulp has a surface area of about 1000 m²/g. Upon drying, the surface area reduces to about 1 m²/g. Even though the lamellae swell upon rewetting, the rewetted pulp has a surface area of only about 100 m²/g. Thus, upon drying, the pores of the never-dried pulp irreversibly collapse. This invention capitalizes on the collapse as a way to trap impregnant in the pulp so that its release will be controlled. It also uses never-dried pulp for faster diffusion of larger chemicals into the microporous structure of the cellulose.

To capitalize on the larger pores in never-dried pulp, it is essential that the pores do not prematurely collapse. With sequential solvent exchange, some pores often are irreparably damaged through collapse. At least five ways are known to reduce pore collapse at the encapsulation stage (i.e., diffusion of impregnant into the pores). First, the capillary pressure forces can be decreased by reducing interfacial tensions in primarily three ways: (1) by use of a surface active material (surfactant), (2) by use of a liquid which develops low interfacial tensions, or (3) by increase of the encapsulation temperature. The capillary pressure forces may be completely eliminated if the solution for encapsulation is miscible with the previous solvent remaining within the cell wall pores. Second, the electrical repulsive forces may be increased by use of materials like anionic surfactants which may increase the surface charge density by being specifically adsorbed onto cellulose structure. Third, the long-range van der Waals attractive forces may be decreased by selecting a solvent, when possible, which minimizes the values of the Hamaker constant between the lamellae and liquid medium. See, e.g., P. HIEMENZ, *PRINCIPLES OF COLLOID AND SURFACE CHEMISTRY*, Marcel-Dekker (1977), 412–418. Fourth, the use of a swelling agent more powerful than water, such as liquid ammonia, formamide, or an aqueous alkaline or acidic solution, will produce more pores in the cell walls. Fifth, steric hindrance may be used to prevent collapse by incorporating bulky molecules into the pores.

To form a controlled release composition, the never-dried pulp is immersed in a solution of impregnant, such as 2,4-dichlorophenoxyacetic acid in toluene, or naphthaleneacetic acid in tetrahydrofuran. Chemical substances having a molecular diameter as large as about 300 angstroms may be used as impregnants for never-dried wood pulp (this dimension being substantially equal to the largest pore of the pulp). Much larger molecules may be used as impregnants with never-dried pulp than with "once-dried" pulp. Therefore, never-dried pulp presents opportunities for much greater use. Other possible impregnants, for example, are methyl nonyl ketone, aspirin, diethyl toluamide, selenium dioxide (in water or ethanol), or citric acid.

Particularly when the solution of impregnant is immiscible in water, solvent exchange steps can be avoided by using a distillation method to include the impregnant into the carrier. For example, the never-dried pulp is directly mixed in a reactor with the water-immiscible solvent, such as n-hexane, toluene, or another suitable hydrocarbon. The mixture is heated to evaporate the water and solvent, which are condensed and collected in a distilling receiver. If required to remove all the water from the reactor, additional solvent is added to the reactor. Solvent can be recycled from the distilling receiver.

In selecting a solvent for the distillation method just described, five factors should be considered. First, a solvent with a higher boiling point is more effective in eliminating water from the pulp. Second, the lower the interfacial tension between the water in the pulp and the solvent, the smaller are the contracting forces developed within the cell pores (which cause pore collapse). Third, the more a solvent reduces the attractive forces (i.e., long-range van der Waals forces) within the cell wall pores, the better the solvent is. Fourth, the higher the surface tension of the solvent, the greater the amount of impregnant trapped when the cell walls collapse upon drying. Fifth, the solvent and water should not form an azeotrope, if other solvents are available.

Suitable solvents may be, for example, toluene, xylene, and other aromatic hydrocarbons; n-hexane, n-octane, and other aliphatic hydrocarbons; ethyl acetate and other esters; carbon tetrachloride and other chlorinated hydrocarbons; diethyl ether and other ethers; and ethyl alcohol and other aliphatic alcohols. Toluene is preferred if the impregnant is reasonably soluble in it.

A surfactant may be added to the reactor mixture to enhance the inclusion of impregnant into the cellulose pulp and to reduce premature pore collapse. A suitable surfactant should be soluble in the water and solvent over a wide range of temperatures, and be stable at high temperatures without sublimation or evaporation.

Because the reactor is operated at the boiling point of the mixture, the solubility of the solute in the mixture can be increased greatly. As the solvent is distilled off, the solute concentration rises, with a resulting increase in the amount of impregnant trapped. Because the pulp is always immersed in solution throughout the inclusion process, the chances of premature pore collapse are diminished in comparison with conventional solvent exchange steps which have alternate stages of immersion and filtration. The distillation method reduces the number of steps ordinarily required in conventional solvent exchange and is superior to solvent exchange, especially when the solvent and fluid in the pores of the carrier are immiscible.

During distillation, the solution of impregnant diffuses through the pulp to displace water otherwise in the pores. After distillation, a second liquid, such as chilled water, is used to wash and to cool the pulp. This second liquid causes the impregnant to crystallize and to precipitate in the pores so that more impregnant will remain in the pulp upon drying. The pulp is then dried to form the controlled release composition.

The impregnated pulp may be formed into mats, sheets, tablets, or the like to allow easier handling and to provide further control of the rate of dispersion of the impregnant from the pulp. A polymer coating, for example, polyvinyl alcohol, polyvinyl acetate, polyethylene glycol, or mixtures thereof, may be added to the tablets to form a film coating as yet another means to control the rate.

EXAMPLE 1

Three grams of never-dried sulfite pulp were immersed in a solution of 100 ml toluene, eight grams of 2,4-dichlorophenoxyacetic acid (useful as a plant growth stimulant or an herbicide), 10 ml water, and 0.02% of the surfactant polyoxyethylene (23) lauryl ether. The solution was distilled in a Dean-Stark distilling receiver until all water was removed. The pulp was filtered and air dried. The dried mat was washed with tetrahydrofuran until all the 2,4-dichlorophenoxyacetic acid was washed from the surface. It was useful as a controlled release composition.

The described embodiments are meant to illustrate the invention rather than to limit it, and are given as examples of the method.

I claim:

1. A method for preparing a controlled release composition containing an impregnant in a microporous carrier which is initially fluid-filled, comprising the steps of:
   (a) immersing the microporous, fluid-filled carrier in a first solution containing the impregnant and a solvent to form a mixture;
   (b) distilling the fluid in the carrier's pores from the mixture to exchange the fluid in the pores of the carrier with the solution; and
   (c) drying the carrier to entrap the impregnant within the carrier structure.

2. The method of claim 1 wherein the carrier is cellulose pulp.

3. The method of claim 1, further comprising the step of washing the pulp with a second solution to precipitate the impregnant, after distilling but before drying.

4. The method of claim 1 wherein the first solution of impregnant contains a surfactant which is soluble in both the solution and the fluid in the carrier.

5. The method of claim 4 wherein the surfactant is a polyoxyethylene lauryl ether.

6. A method for preparing a controlled release composition containing an impregnant in a cellulose pulp initially containing water, comprising the steps of:
   (a) immersing never-dried pulp in a first solution containing the impregnant and a solvent to form a mixture of the pulp and the solution;
   (b) distilling the water from the mixture to exchange water in the pulp with the solution; and
   (c) drying the pulp to entrap the impregnant within the pulp structure.

7. The method of claim 6 wherein the solvent of the solution is immiscible with water.

8. The method of claim 7 wherein the solvent is toluene.

9. The method of claim 7 wherein the solvent is n-hexane.

10. The method of claim 6, further comprising the step of recycling solvent during the distilling step.

11. The method of claim 6 or 10, further comprising the step of washing the pulp with a second solution to precipitate the impregnant, after distilling but before drying.

12. The method of claim 6, further comprising the step of applying a polymer coating to the pulp after drying.

13. A method for preparing a controlled-release composition containing an impregnant in a microporous carrier which was initially fluid-filled, comprising the steps of:
   (a) contacting never-dried pulp with a solution containing the impregnant and a solvent to form a mixture of the pulp and solution;
   (b) distilling the mixture to evaporate the water within the never-dried pulp and to exchange the solution with the water; and
   (c) removing the solvent from the pulp to trap the impregnant within the pulp structure;
wherein the impregnant is substantially insoluble in water and wherein the solvent is substantially immiscible with water.

14. A method for preparing a controlled-release composition containing an impregnant in a microporous carrier which was initially fluid-filled, comprising the steps of:
   (a) contacting the microporous, fluid-filled carrier with a solution containing the impregnant and a solvent to form a mixture of the carrier and solution;
   (b) distilling the fluid in the carrier's pores from the mixture to exchange the fluid in the pores of the carrier with the solution; and
   (c) entrapping the impregnant within the pores to form a controlled-release composition.

* * * * *